United States Patent
Hsieh et al.

(10) Patent No.: US 8,483,804 B2
(45) Date of Patent: Jul. 9, 2013

(54) METHOD AND APPARATUS FOR RECONSTRUCTING IMAGES OF MOVING STRUCTURES BASED ON MOTION CYCLE TEMPORAL DATA

(75) Inventors: Jiang Hsieh, Brookfield, WI (US); Xiangyang Tang, Waukesha, WI (US); Baojun Li, Waukesha, WI (US); Darin Robert Okerlund, Muskego, WI (US)

(73) Assignee: General Electric Company, Schenectady, NY (US)

( * ) Notice: Subject to any disclaimer, the term of this patent is extended or adjusted under 35 U.S.C. 154(b) by 1340 days.

(21) Appl. No.: 11/825,900

(22) Filed: Jul. 10, 2007

(65) Prior Publication Data
US 2009/0018435 A1 Jan. 15, 2009

(51) Int. Cl.
*A61B 5/05* (2006.01)
(52) U.S. Cl.
USPC ........... 600/428; 600/413; 600/425; 382/128; 382/294
(58) Field of Classification Search
USPC .................. 600/407, 425, 428; 382/128, 130, 382/276, 294; 345/419, 427, 629, 633, 634
See application file for complete search history.

(56) References Cited

U.S. PATENT DOCUMENTS
6,351,514 B1 * 2/2002 Besson ........................... 378/15
6,639,965 B1 * 10/2003 Hsieh et al. ...................... 378/8

OTHER PUBLICATIONS

Keller et al. The Angular Difference Function and Its Application to Image Registration. IEEE Transactions on Pattern Analysis and Machine Intelligence. 27(6):969-976. 2005.*
Jiang Hsieh et al., Step-and-shoot data acquisition and reconstruction for cardiac x-ray computed tomography, 4236 Med. Phys. 33 (11), Nov. 2006.

* cited by examiner

*Primary Examiner* — Parikha Mehta
(74) *Attorney, Agent, or Firm* — The Small Patent Law Group; Dean D. Small (57) ABSTRACT

A method for reconstructing images of structures undergoing physiological motion comprises acquiring a first volume of data over a first motion cycle. The first volume comprises a first overlap volume. A second volume of data is acquired over a second motion cycle and comprises a second overlap volume. The first and second overlap volumes comprise like anatomical regions with respect to each other. A reconstructed volume of data is formed based on temporal data within the first and second overlap volumes.

22 Claims, 7 Drawing Sheets

METHOD AND APPARATUS FOR RECONSTRUCTING IMAGES OF MOVING STRUCTURES BASED ON MOTION CYCLE TEMPORAL DATA

BACKGROUND OF THE INVENTION

This invention relates generally to diagnostic imaging and, more particularly, to acquiring and reconstructing image data of structures subject to physiological motion using a computed tomography (CT) apparatus.

Helical cardiac acquisition has historically had the problem of high radiation dose to patients and lack of arrhythmia management. During a helical scan, the projection of x-ray toward a patient and table translation through the gantry opening are continuous. A step-and-shoot (SAS) acquisition technique has been used to overcome some of the problems associated with helical scanning, such as by significantly reducing the dose by, for example, more than a factor of two over a wide range of heart rates when scanning the cardiac region. In SAS mode, the patient table remains stationary while the x-ray tube and gantry rotate about the patient and the projections are collected over a minimum half-scan range. The table is indexed between acquisitions to move the patient with respect to the x-ray tube and gantry.

Currently, for cardiac scanning the SAS mode and other CT cardiac acquisition modes typically use the patient's electrocardiogram (ECG) signal to control data acquisition and reconstruction. Based on the R-R intervals, either a percentage delay or a fixed delay is used to determine the optimal acquisition and reconstruction windows. The ECG, however, represents the electrical signal of the heart and not the mechanical state of the heart. As a result, suboptimal gating often results as the heart rate (and thus motion of the heart) varies from beat to beat, sometimes to a large degree. Due to the variation, artifacts can result during reconstruction. Artifacts may be seen as discontinuities or abrupt changes in vessels and other anatomical structures that do not reflect accurate anatomical structure. Artifacts may also result from other physiological motion, such as respiration and involuntary motions of the patient when imaging structures within the patient other than the heart.

Therefore, a need exists for improved acquisition and gating techniques to improve CT imaging of structures subject to movement within a patient.

BRIEF DESCRIPTION OF THE INVENTION

In one embodiment, a method for reconstructing images of structures undergoing physiological motion comprises acquiring a first volume of data over a first motion cycle. The first volume comprises a first overlap volume. A second volume of data is acquired over a second motion cycle and comprises a second overlap volume. The first and second overlap volumes comprise like anatomical regions with respect to each other. A reconstructed volume of data is formed based on temporal data within the first and second overlap volumes.

In another embodiment, a Computed Tomography (CT) system for acquiring cardiac data comprises an x-ray source configured to project x-rays at a subject to be scanned. An x-ray detector array is configured to detect x-rays projected by the x-ray source and attenuated by the subject, and a table holds the subject with respect to the x-ray source and the x-ray detector. A computer is configured to acquire a first volume of data over a first motion cycle and a second volume of data over a second motion cycle. The first and second volumes have first and second overlap volumes, respectively, that comprise common anatomical regions of the subject. The computer is configured to combine the first and second volumes based on the first and second overlap volumes.

In yet another embodiment, a method for acquiring images of a subject comprises acquiring at least two volumes of data that comprise at least a portion of a structure undergoing physiological motion. Each of the at least two volumes of data are acquired over a different physiological motion cycle and comprise at least one overlap volume that has common anatomical data with an adjacent volume of data. At least first and second overlap volumes that have common anatomical data are compared to one another to identify at least one temporal shift indicating a best match between the motion cycles associated with the at least first and second overlap volumes. At least two volumes of data are combined based on at least one temporal shift.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

Figure 1:
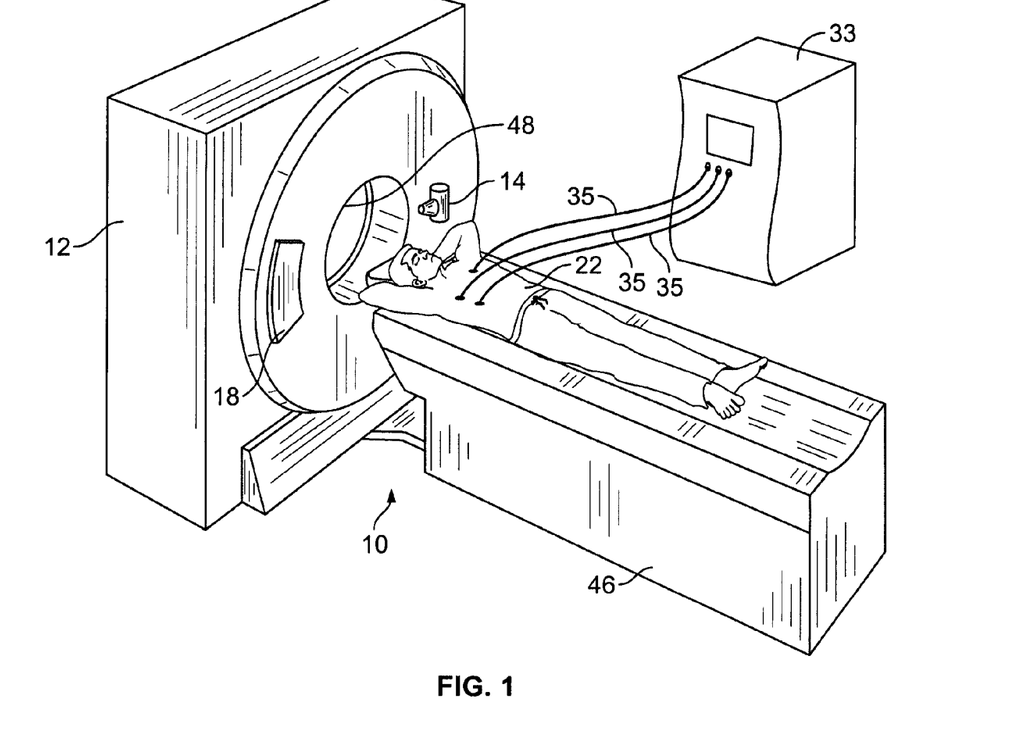
FIG. 1 illustrates a perspective view of a CT system formed in accordance with an embodiment of the present invention.
Figure 2:
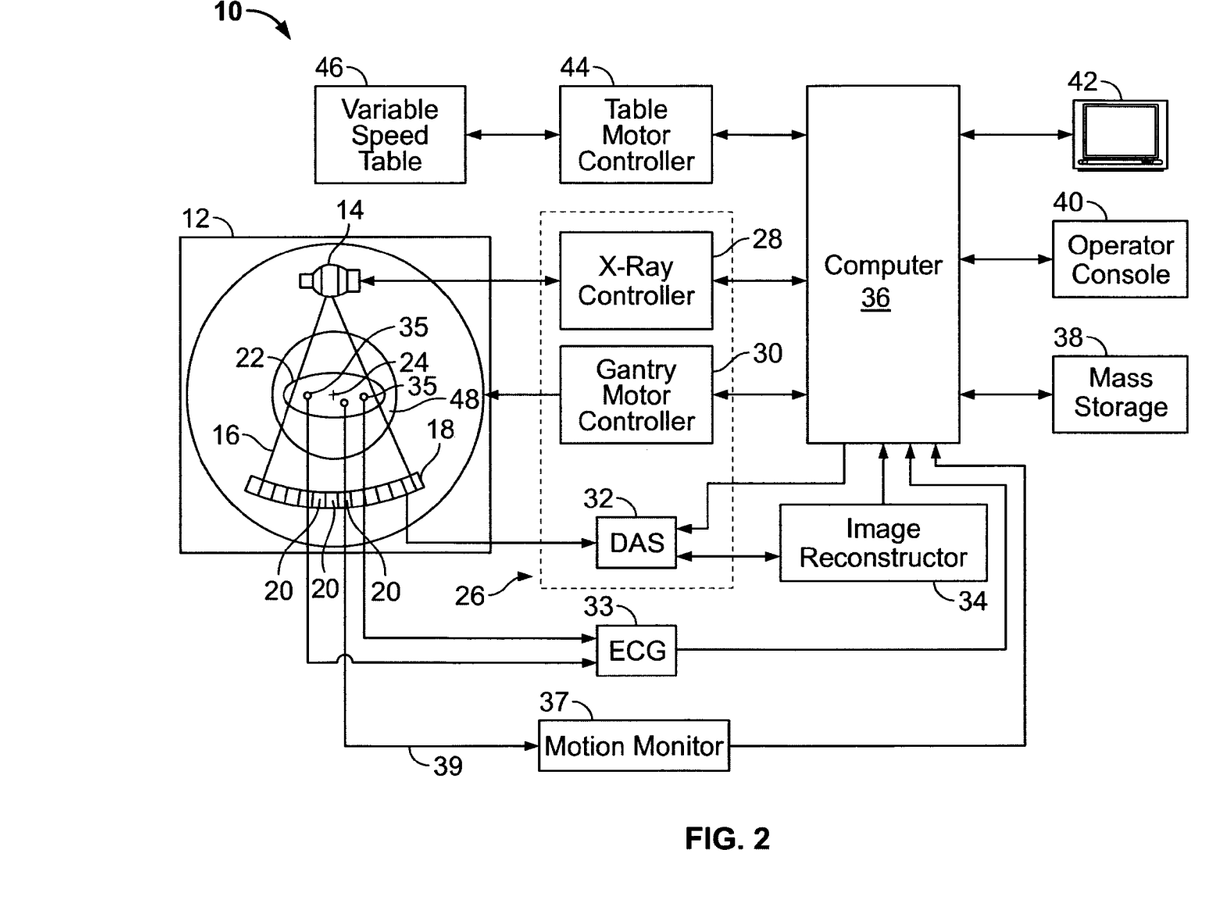
FIG. 2 illustrates a block schematic diagram of the system of FIG. 1 formed in accordance with an embodiment of the present invention.

FIGS. 1 and 2 illustrate a computed tomography (CT) imaging system 10. The system 10 includes a gantry 12 having an x-ray source 14 that projects a beam of x-rays 16 toward a detector array 18 that is on the opposite side of the gantry 12. Detector array 18 is formed by a plurality of detectors 20 that together sense the projected x-rays that pass through a medical subject 22. In one embodiment, detector array 18 has 64 rows of detectors for the acquisition of 64 slices of data in a single gantry rotation. Each detector 20 produces an electrical signal that represents the intensity of an impinging x-ray beam and hence the attenuated beam as it passes through the subject 22. During a scan to acquire x-ray projection data, the gantry 12 and the components mounted thereon rotate about a center of rotation 24.

Rotation of the gantry 12 and the operation of the x-ray source 14 are governed by a control module 26 of the CT system 10. Control module 26 includes an x-ray controller 28 that provides power and timing signals to the x-ray source 14 and a gantry motor controller 30 that controls the rotational speed and position of gantry 12. In step-and-shoot (SAS) mode, the x-ray source 14 and detector array 18 rotate about the subject 22, while the subject 22 is held stationary on the table 46. The detector array 18 has an associated field of view (FOV) that is based, at least in part, on a projection angle that is related to the amount of rotation of the x-ray source 14 and the detector array 18.

A data acquisition system (DAS) 32 in control module 26 samples analog data from detectors 20 and converts the data to digital signals for subsequent processing. As will be described below, computer 36 may also receive ECG signals from an ECG apparatus 33 connected to the subject 22 via leads 35 to acquire cardiac data of the subject 22. The computer 36 correlates the ECG signals to determine the phases of the cardiac region. The ECG apparatus 33 may obtain an ECG recording of the subject 22 before scanning commences such that data acquisition can be timed to occur during quiescent periods between R-peaks of a cardiac cycle. During these quiescent periods, the heart is relatively still and, therefore, the acquisition of data can occur during these portions of the cardiac cycle to minimize motion artifacts in the final reconstructed image. An image reconstructor 34 receives sampled and digitized x-ray data from the DAS 32 and performs high-speed reconstruction. The reconstructed image is applied as an input to the computer 36 that stores the image in a mass storage device 38.

A motion monitor 37 may also be connected to the subject 22 via lead(s) 39 to acquire physiological motion data of the subject 22. The motion monitor 37 may obtain respiration data, involuntary motion by the subject 22, and/or neural, digestive and peristaltic motion, for example. Data acquisition may be timed based on the detected motion and/or the image reconstructor 34 may use the motion data when forming a reconstructed image. Typically, a subject 22 may be asked to hold their breath when CT data is being acquired. In one embodiment, by acquiring the CT data without breath holding such that the data includes the respiration motion, reconstructed images may be more easily registered and/or combined with images from other modalities that take much longer to acquire the radiation data, such as Positron Emission Tomography (PET), which may acquire data for 10-15 minutes. For example, CT images may be registered with PET images by matching breath cycles.

The computer 36 also receives commands and scanning parameters from an operator via console 40 that has a keyboard or other input device(s). An associated display 42 allows the operator to observe the reconstructed image and other data from computer 36. The operator supplied commands and parameters are used by computer 36 to provide control signals and information to DAS 32, x-ray controller 28, ECG apparatus 33, motion monitor 37 and gantry motor controller 30. In addition, the computer 36 operates a table motor controller 44 that controls a motorized table 46 to position the subject 22 and gantry 12. Particularly, the table 46 moves portions of the subject 22 through a gantry opening 48.

Figure 3:
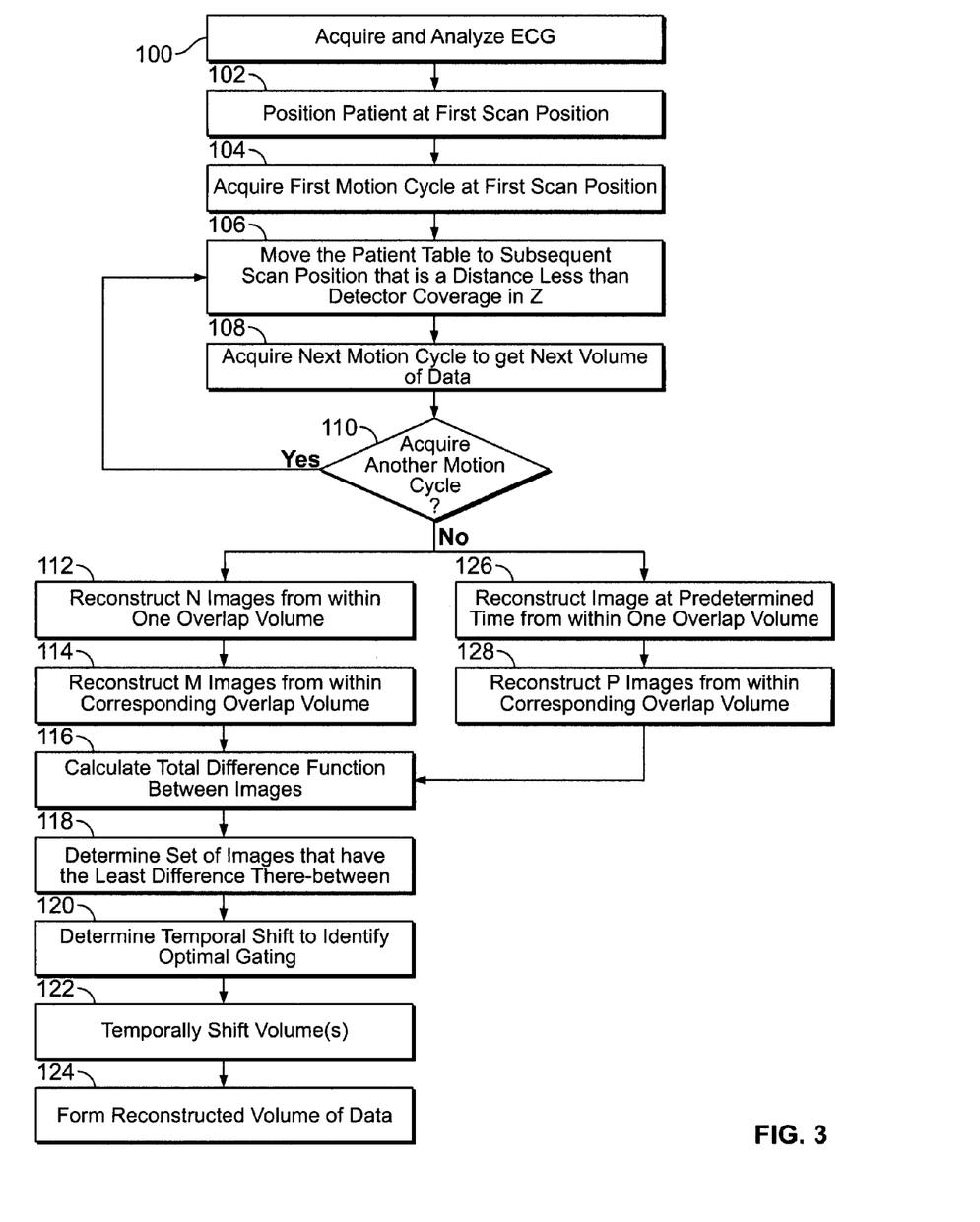
FIG. 3 illustrates a method for cardiac image reconstruction based on optimal gating and temporal window adjustment in accordance with an embodiment of the present invention.

FIG. 3 illustrates a method for cardiac image reconstruction based on optimal gating and temporal window adjustment. Although the method is discussed primarily with respect to cardiac image reconstruction, it should be understood that other organs and structures within the subject 22 may be reconstructed based on other physiological motion within the subject 22 such as respiration. A subject 22 is positioned on the table 46 and interconnected with the leads 35 to the ECG apparatus 33 (or via the lead(s) 39 to the motion monitor 37) as previously discussed. At 100, an ECG may be acquired by the ECG apparatus 33 and analyzed by the computer 36 prior to the CT data acquisition. The computer 36 and/or an operator may evaluate the ECG to determine the stability and variability of the patient's heart cycles. If the heart rate is variable beyond a predetermined threshold, the computer 36 may determine that a greater amount of data should be acquired, such as over a larger projection angle. Therefore, the computer 36 and/or operator may determine, based at least in part on the particular ECG data of the patient, an acquisition protocol that acquires enough data to allow the desired temporal window adjustment. Conversely, less data may be acquired if the heart rate is more regular. This may decrease the patient's exposure to radiation.

In addition, scan data may be acquired at a particular prescribed position or phase within the cardiac or heart cycle, such as based on the R-R intervals. For example, the computer 36 may correlate the ECG signals to determine the phases of the subject's heart motion. In one embodiment, data acquisition is timed to occur between R-peaks of the cardiac cycle when the heart is relatively still and motion artifacts may be minimized. Scan data may also be acquired at other prescribed positions within other physiological cycles.

At 102 the subject 22 is positioned at a first scan position to image a first portion of the heart. The first (and subsequent) scan positions may identify the position of the table 46 with respect to the x-ray source 14 and detector array 18. In one embodiment, the heart is scanned from one side to the other. Optionally, the heart may be scanned such that non-adjacent portions are scanned with consecutive acquisitions. For a detector coverage in z of 40 millimeter (mm), the entire volume of the heart can typically be scanned in four or five scan positions, acquiring four or five adjacent overlapping volumes. At 104 the computer 36 acquires image data over a first motion cycle, such as a first cardiac or heart cycle, at the first scan position. In this example, the SAS acquisition technique is used, although it should be understood that the data may also be acquired using the helical acquisition technique or other known technique. Also, the first motion cycle may be based on a different motion, such as a breath cycle as determined by the motion monitor 37.

Figure 4:
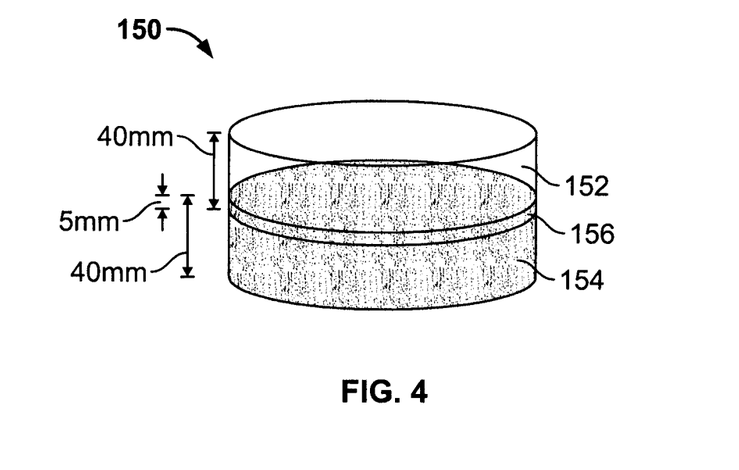
FIG. 4 illustrates overlapped volumes of data wherein each of the volumes of data is based on a different motion cycle in accordance with an embodiment of the present invention.

FIG. 4 illustrates overlapped volumes of data 150 wherein each of the volumes of data is based on a different motion cycle. A first volume of data 152 is reconstructed based on, for example, a first cardiac cycle and covers 40 mm in z. The first volume of data 152 may include data acquired over a 50 centimeter (cm) FOV of the detector array 18. Larger or smaller projection angles may be used such that the FOV is increased or decreased, respectively, to ensure that adequate data is acquired for the temporal shift and/or to minimize radiation exposure. Optionally, the computer 36 may determine (at this scan position and subsequent scan positions) if the acquired data is valid. Therefore, additional scan data may be acquired, if necessary, at the first scan position.

At 106, the computer 36 indexes the table 46 to a second or next scan position that is less than the total distance coverage in z. For example, the first volume of data 152 covers 40 mm in z, and thus the table 46 is indexed a distance less than 40 mm, such as 35 mm, so that the subsequent data acquisition results in a volume that overlaps the previous acquisition in z. Alternatively, the table 46 may be moved to a different position if adjacent volumes are being acquired with non-consecutive acquisitions.

At 108, the computer 36 acquires image data over a second motion cycle at the second scan position. A second volume of data 154 as shown in FIG. 4 covers 40 mm in z and represents reconstructed data based on the second image cycle. An overlap volume 156 is also shown and represents the same anatomy or anatomical region of the subject 22 within both of the first and second volumes of data 152 and 154. The second motion cycle (e.g. cardiac cycle) may be acquired at the same position or phase within the heart cycle as the first motion cycle, or may be acquired during a different phase determined to better image particular anatomy. Typically, the first and second cardiac cycles are not adjacent cardiac cycles with respect to each other.

At 110 the computer 36 determines whether another motion cycle is to be collected. If yes, the method returns to 106. As discussed previously, four to five acquisitions of data may be needed to image the entire heart. Other numbers of acquisitions may be needed to image other structures such as the lungs or liver. If no more data is to be collected, the method passes to 112 or 126, each of which illustrates a different exemplary processing technique.

Figure 5:
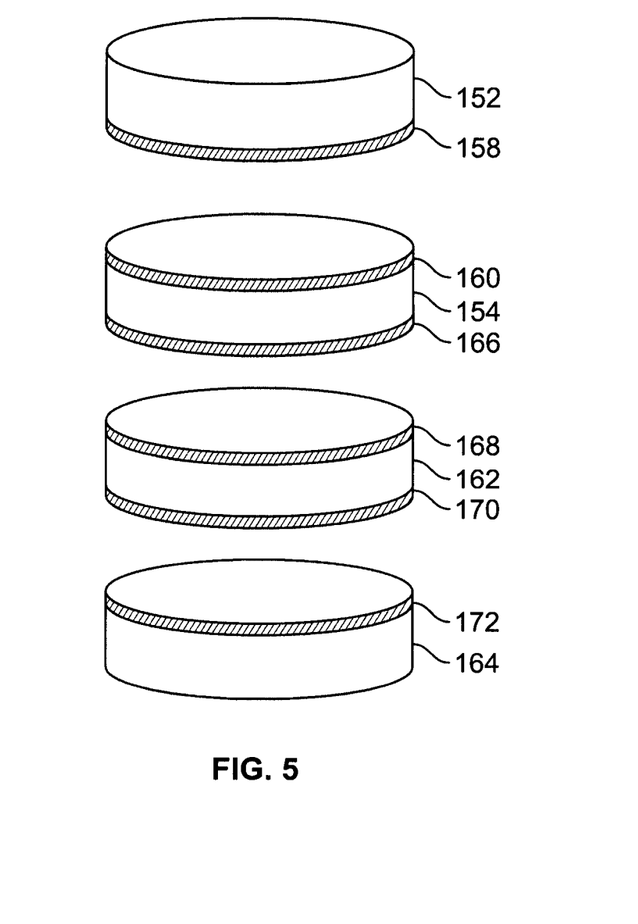
FIG. 5 illustrates multiple volumes of data acquired to cover the cardiac anatomy of the subject in accordance with an embodiment of the present invention.

FIG. 5 illustrates multiple volumes of data acquired to cover the cardiac anatomy of the subject 22. The first and second volumes of data 152 and 154 are illustrated separately from each other. The overlap volume 156 (of FIG. 4) is indicated as first overlap volume 158 within the first volume of data 152 and as second overlap volume 160 within the second volume of data 154. Additionally, third and fourth volumes of data 162 and 164 are illustrated. The second and third volumes of data 154 and 162 include third and fourth overlap volumes 166 and 168, respectively, and the third and fourth volumes of data 162 and 164 include fifth and sixth overlap volumes 170 and 172, respectively. The third and fourth overlap volumes 166 and 168 are of the same anatomical region or structures, such as of the same 5 mm within the subject 22, and the fifth and sixth overlap volumes 170 and 172 are of the same anatomical region.

Returning to FIG. 3, in general, the image reconstructor 34 (of FIG. 2) reconstructs at least one image from corresponding overlap volumes, such as from each of the first and second overlap volumes 158 and 160, and then compares the images between the corresponding overlap volumes to determine the images that are the least different physiologically with respect to each other. Images that have the least amount of difference represent the points in time within the two motion cycles where the mechanical state of the structure undergoing the physiological motion is the closest to being the same.

In one embodiment, multiple images from corresponding overlap volumes are compared to each other to determine the minimum difference. At 112 the image reconstructor 34 reconstructs a set of N images at preset times from within the first overlap volume 158 of the first volume of data 152. The preset times represent different temporal windows or times within the first overlap volume 158. Alternatively, the operator may define and/or change the preset times and/or the number N of images to be reconstructed. At 114 the image reconstructor 34 reconstructs a set of M images at preset times from within the second overlap volume 160 of the second volume of data 154. The number of N and M images may be the same or different from each other, and the preset times associated with each of the N and M images may be the same or different from each other.

At 116, the computer 36 calculates a total difference function $\xi(t_1, t_2)$ between images from the first overlap volume 158 and images from the second overlap volume 160. For example, a first image, $f_1(x, y, z, t_1)$, may be reconstructed from the first overlap volume 158 and a second image, $f_2(x, y, z, t_2)$, may be reconstructed from the second overlap volume 160. The total difference function, $\xi(t_1, t_2)$, is then calculated using Equation (Eq.) 1 to characterize the cardiac motion between the two images:

$$\xi(t_1, t_2) = \sum_{z=1}^{M} \sum_{x=1}^{N} \sum_{y=1}^{N} |w_1(x, y, z) f_1(x, y, z, t_1) - w_2(x, y, z) f_2(x, y, z, t_2)| \qquad \text{Eq. 1}$$

In Eq. 1, $t_1$ and $t_2$ represent the temporal windows for images generated in the first and second volumes of data 152 and 154, respectively, z is the z location of the reconstructed images, and x and y are the image pixel indexes. The weighting functions, $w_1(x,y,z)$ and $w_2(x,y,z)$, are used to minimize cone beam and motion artifacts, or to optimize the anatomy outside the cardiac region. The total difference function $\xi(t_1, t_2)$ may be determined between all of the images of 112 and 114.

At 118, the computer 36 determines a set of images (e.g. one image from each of the first and second overlap volumes 158 and 160) that have the least difference with respect to each other. For cardiac imaging, each of the images within the set of images has an associated time that defines the image's location within the acquisition ECG window. For example, by reconstructing images with different temporal windows from each of the first and second volumes of data 152 and 154 at different values of $t_1$ and $t_2$, a two-dimensional curve of the total difference function $\xi(t_1, t_2)$ may be generated. The best "phase match" may then be determined between the two cardiac acquisitions by locating the minimum value of the total difference function.

Figure 6:
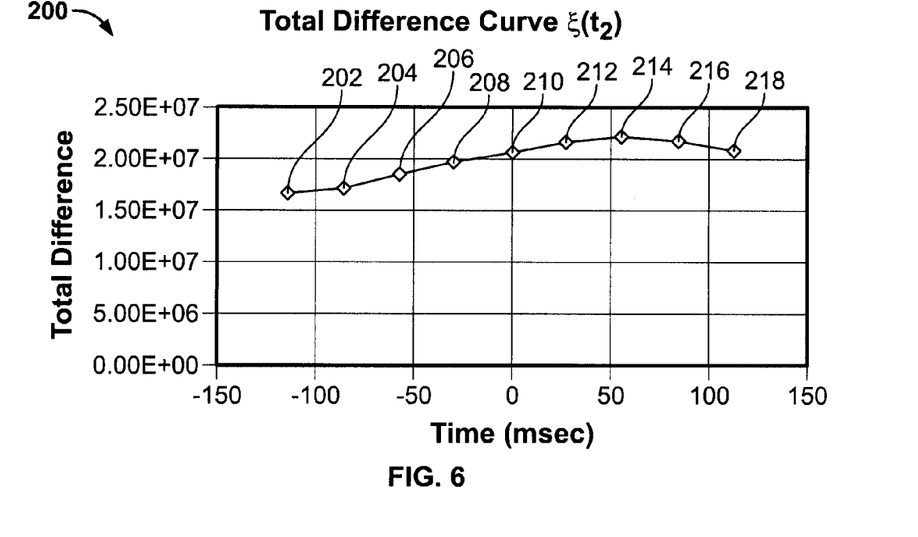
FIG. 6 illustrates a one-dimensional total difference curve formed in accordance with an embodiment of the present invention.

FIG. 6 illustrates a one-dimensional total difference curve 200 comparing multiple images of the second overlap volume 160 to one image of the first overlap volume 158. The curve 200 of $\xi(t_2)$ has been generated by fixing the time $t_1$ of the reconstructed image within the first overlap volume 158 to 0 millisecond (msec), wherein the time $t_1$ is based on the ECG indicated temporal window (or other physiological indicated temporal window, such as a breath cycle). Therefore, the horizontal axis indicates the time difference between the ECG indicated temporal window and the relative times of potential, actual reconstruction windows. The reconstructed image at 0 msec of the first overlap volume 158 is compared to a plurality of images from the second overlap volume 160 that are located at various times with respect to $t_1$. Total differences 202-218 corresponding to the various times with respect to $t_1$ are shown.

As discussed previously, the first and second overlap volumes 158 and 160 have the same patient anatomical structures and may correspond to the same ECG gated portion of the heart cycle. However, differences between the images of the first and second overlap volumes 158 and 160 at the same temporal location as indicated by the ECG may be attributed to the different motion characteristics between the heart and the surrounding organs, as well as variability between the heart cycles. Therefore, a better match may be created between the first and second volumes of data 152 and 154 by temporally shifting the data prior to combining the volumes. The temporal shift provides an optimal gating that may be used when combining the multiple volumes of cardiac data or other cycles of physiological motion data.

At 120 of FIG. 3, the computer 36 determines a temporal shift to identify the optimal gating between the first and second volumes of data 152 and 154 based on the times or locations associated with the minimum value or least difference. Referring to FIG. 6, the 0 msec point on the horizontal axis corresponds to the total difference 210 which is the difference between images from the first and second overlap volumes 158 and 160 that have the same temporal location of 0 msec as indicated by the ECG acquisition window. However, the minimum value of total difference is illustrated by the total difference 202 that occurs at a time that is more than 100 msec away from the 0 msec position. Therefore, the reconstructed image at t=0 msec from the first overlap volume 158 is a better match to the reconstructed image of the second overlap volume 160 corresponding to the total difference 202, and thus a temporal shift of approximately 115 msec may be determined.

At 122 of FIG. 3, the image reconstructor 34 performs a temporal shift based on the identified time(s) of 120. At 124, the image reconstructor 34 forms a reconstructed volume of data based on temporal data within the first and second overlap volumes 158 and 160 that includes both of the first and second volumes of data 152 and 154. The temporal shift may be applied to one or both of the first and second volumes of data 152 and 154. For example, a temporal shift in one direction in time may be applied to the first volume of data 152 while a temporal shift in an opposite direction in time may be applied to the second volume of data 154 to achieve a larger shift than may be accomplished in a single direction.

The above discussion concerns the temporal shift between the first and second volumes of data 152 and 154. In a similar fashion, the temporal shift between second and third volumes of data 154 and 162, and between third and fourth volumes of data 162 and 164 can be determined. As is often the case, the amount of temporal shift between multiple volumes may not be consistent, and an optimum $t_1$, $t_2$ that may be used for combining only the first and second volumes of data 152 and 154 may not be the optimum $t_1$, $t_2$ when combining the first, second and third volumes of data 152, 154 and 162. For example, a first temporal shift for the first and second volumes of data 152 and 154 may require a temporal shift of +10 ms for the second volume of data 154, while a second temporal shift (between second and third volumes of data 154 and 162) may require a temporal shift of +15 ms for the second volume of data 154. It is desirable to minimize the overall difference between all volumes. For example, if the temporal shift for the second volume of data 154 is set to be +15 ms, then the temporal shift for the first volume of data 152 may be adjusted accordingly. In other words, the sum of all ξ (as defined in Eq. 1) is minimized for the entire heart region, thus minimizing the overall temporal shift. It should be understood that other different global optimization processes can be used.

In another embodiment, volumes of data may be combined based on a predetermined time within the acquisition window. The predetermined time may be determined by the image reconstructor 34 or computer 36 based on the ECG data, breath data, other physiological motion data, or may be identified by an operator. At 126, the image reconstructor 34 may reconstruct an image from one of the overlap volumes. In this example, the image reconstructor 34 reconstructs an image from within the first overlap volume 158 at a predetermined time within the ECG defined acquisition window, such as at t=0 msec as illustrated in FIG. 6. At 128, the image reconstructor 34 reconstructs P images from within the second overlap volume 160.

The method passes to 116 where the computer 36 uses Eq. 1 to determine the total difference function between the image from the first overlap volume 158 and the P images from the second overlap volume 160. At 118 the computer 36 determines the set of images that have the least difference therebetween, and optimal gating (at 120) and temporal shift (at 122) are determined as previously discussed.

In yet another embodiment, the computer 36 may iteratively determine the number of images and/or timing between the images based on differences between two images within the same volume. For example, two images from the first overlap volume 158 may be generated with a timing difference of 20 ms there-between. If the difference between the two images is relatively small, another image having a relatively larger timing difference, such as 50 ms, may be generated. However, if the difference between the two images is relatively large, another image having a relatively smaller timing difference, such as 10 ms, may be generated.

In another example, when combining more than two volumes of data the computer 36 may reconstruct images based on a predetermined time (at 126) within the motion cycle. It should be understood that other methods may be used to compare and iteratively optimize gating when combining more than two consecutive volumes.

For cardiac reconstruction, CT systems 10 often employ the half-scan algorithm. When combined with the Feldkamp, Davis and Kress (FDK) cone beam algorithm, the reconstruction produces clinically acceptable image qualities while keeping the computational complexity to a minimum. The FDK-based half-scan algorithm can be described by the following set of equations:

$$f(x, y, z) = \frac{1}{2}\int_0^{\pi+2\gamma_m}\left(\frac{D}{D+y'}\right)^2 d\beta \times \int_{-\infty}^{\infty}\frac{D}{\sqrt{D^2+s^2+v^2}}w(\gamma, \beta)p(\gamma, \beta, \alpha)h(\gamma'-\gamma)d\gamma \qquad \text{Eq. 2}$$

where $w(\gamma, \beta)$ is the well-known half-scan weight:

$$w(s, \beta) = 3\theta^2(\gamma, \beta) - 2\theta^3(\gamma, \beta) \qquad \text{Eq. 3}$$

and $$\theta(\gamma, \beta) = \begin{cases} \dfrac{\beta}{2\gamma_m - 2\gamma}, & 0 \le \beta < 2\gamma_m - 2\gamma, \\ 1, & 2\gamma_m - 2\gamma \le \beta < \pi - 2\gamma, \\ \dfrac{\pi + 2\gamma_m - \beta}{2\gamma_m + 2\gamma} & \pi - 2\gamma \le \beta < \pi + 2\gamma_m. \end{cases}$$

Here, D is the source to iso-center distance. The reconstruction formula uses projection samples over the entire $\pi+2\gamma_m$ projection range. In many cardiac studies, only $\pi+2\gamma_m$ projection data is collected to minimize the dose to patients. As a result, when using the Eq. 2 and 3, the available temporal reconstruction window becomes fixed once the data is collected.

Figure 7:
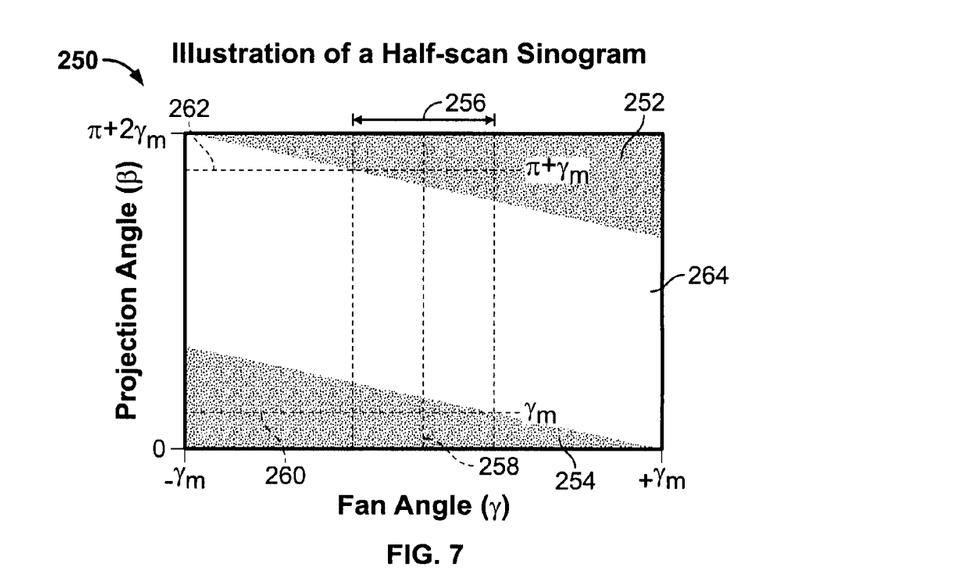
FIG. 7 illustrates a sinogram for one detector row within the detector array in accordance with an embodiment of the present invention.

As discussed in FIG. 3, to accomplish the optimal gating, images are generated or reconstructed at different temporal windows. The following discusses the reconstruction of cardiac data that allows shifting of the temporal window, although it should be understood that the reconstruction applies to other structures undergoing physiological motion. FIG. 7 illustrates a sinogram 250 for a particular detector row within the detector array 18. By way of example, the sinogram 250 may be built as the x-ray source 14 and detector array 18 rotate from one projection angle to the next during the acquisition of the image data associated with one volume of data. As the relationship is identical over all detector rows, only one such sinogram 250 will be discussed. The entire sinogram 250 covers an angular range of $\pi+2\gamma_m$ projection angle and represents data collected for a 50 cm acquisition FOV, as represented by $-\gamma_m$ to $+\gamma_m$. A region of measured samples 264 is shown, and two regions of redundant samples are shown by shaded regions 252 and 254. Therefore, redundant data is collected within a single scan (such as within the data collected to form the first volume of data 152).

The conjugate sample for $(+\gamma_m, 0)$ is $(-\gamma_m, \pi+2\gamma_m)$, and therefore the $\pi+2\gamma_m$ projection angle is needed for half-scan reconstruction over the 50 cm FOV. As $\gamma_m$ reduces, corresponding to a reduced FOV, the angular range reduces as can be seen by the redundant samples in the shaded regions 252 and 254. For example, when $\gamma_m=0$, indicated with line 258, only $\pi$ projection angle is required for a complete reconstruction.

A smaller FOV is needed for cardiac imaging, however, such as region 256 which is a 25 cm FOV. The region 256 corresponds to the collection of data over $\pi+\gamma_m$ projection angle as shown by lines 260 and 262. While acquiring data over the region 256 provides images of the cardiac anatomy, acquiring data over a larger region, such as the entire 50 cm FOV or over the entire $\pi+2\gamma_m$ projection angle, provides the data needed for the temporal shift.

Figure 8:
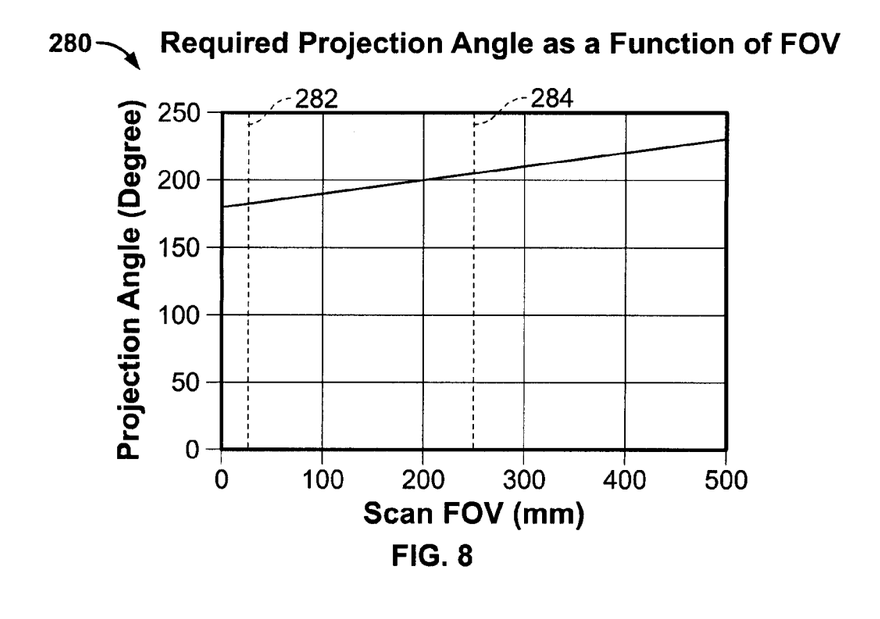
FIG. 8 illustrates a plot of the projection angular span as a function of reconstruction FOV in accordance with an embodiment of the present invention.

FIG. 8 illustrates a plot 280 of the projection angular span as a function of reconstruction FOV. This example is based on a particular CT system 10 geometry and speed of rotation, and it should be understood the change in angular range and amount of available temporal shift may be different when compared to other CT systems. Approximately 235 degrees of data is needed for the full 50 cm FOV (given 0.35 seconds per gantry revolution). Line 284 indicates an angular range associated with 25 cm FOV, such as the region 256 of FIG. 7. For imaging only cardiac structures wherein a typical heart size is 12 cm in diameter, an angular range of 192.7 degrees is needed as indicated by line 282. This is a reduction of 42.3 degrees, which corresponds to more than 41 msec in time. Therefore, if the cardiac image can be reconstructed using a set of projections that is less than the total set of projections, the reconstruction window can be shifted in the temporal domain. In this example, the amount of temporal shift available is approximately 41 msec.

Figure 9:
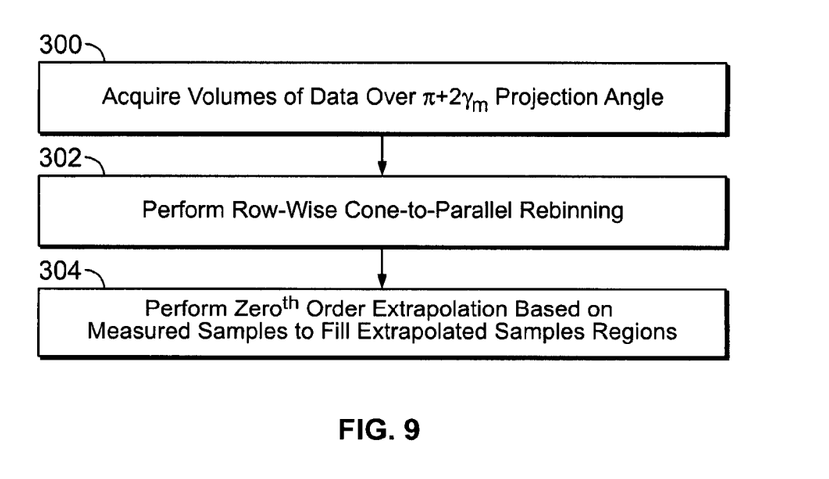
FIG. 9 illustrates a method for reconstructing the heart region based on the minimum projection angle associated with the cardiac region in accordance with an embodiment of the present invention.

FIG. 9 illustrates a method for reconstructing the heart region based on the minimum projection angle associated with the cardiac region. At 300, the computer 36 acquires the first volume of data 152, second volume of data 154, and subsequent volumes of data, over $\pi+2\gamma_m$ projection angle. The volumes overlap in z as previously discussed. At 302, the computer 36 performs row-wise cone-to-parallel rebinning to form rebinned data. In other words, the computer 36 interpolates a set of cone beam projections, $p(\gamma, \beta, \alpha)$, to a set of tilted parallel beam projections $q(t, \theta, \alpha)$, where t represents the distance of the parallel ray to the iso-center, and $\theta$ represents the parallel beam angle. Therefore, the original sinogram 250 in the $\gamma$-$\beta$ domain is mapped to a sinogram in the t-$\theta$ domain.

Figure 10:
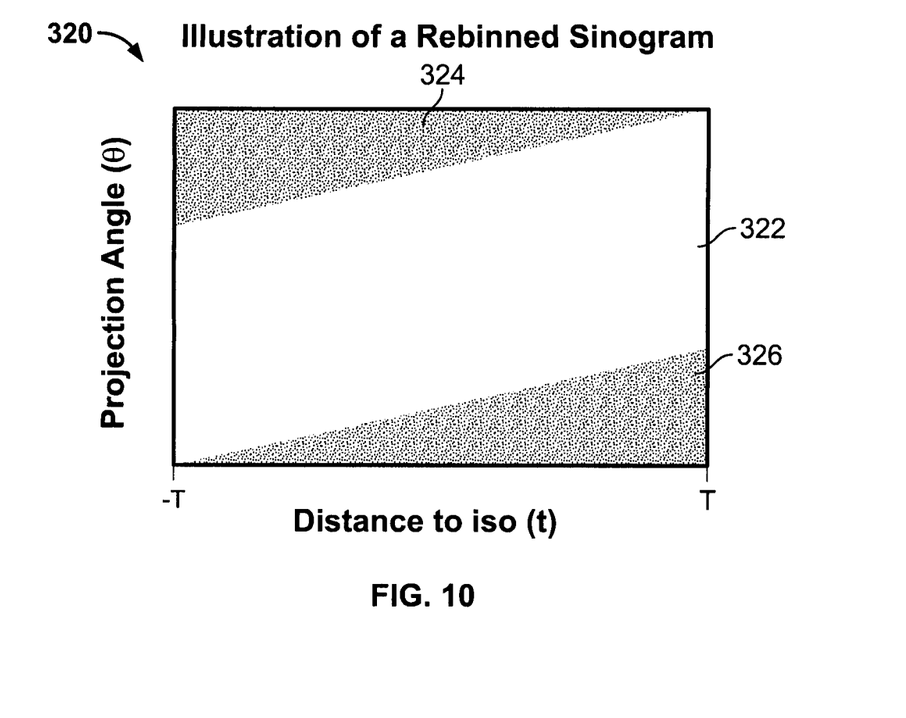
FIG. 10 illustrates the sinogram of FIG. 7 mapped to a sinogram in the t-θ domain in accordance with an embodiment of the present invention.

FIG. 10 illustrates the sinogram 250 (of FIG. 7), mapped to a sinogram 320 in the t-$\theta$ domain. The sinogram 250 is represented as measured samples region 322. At 304 of FIG. 9, the computer 36 performs a zero$^{th}$ order extrapolation to the measured samples region 322 to fill (populate) extrapolated samples regions 324 and 326 of the sinogram 320. The extrapolation may be performed by replicating the measured samples at the boundary along $\theta$. As the measured samples along the boundary represent projection samples of a single cone beam view, artifacts resulting from the filtering operation are unlikely. It should also be understood that many other extrapolation techniques, such as 1$^{st}$ order or higher order extrapolations may be used rather than the zero$^{th}$ order extrapolation. Alternatively, extrapolation or interpolation using conjugate samples can be used. The conjugate samples are illustrated in the shaded regions 252 and 254 of FIG. 7.

The extrapolation enlarges the original angular range from $\pi+2\gamma_m$ (in cone beam) to $\pi t+4\gamma_m$ (in tilted parallel beam). Therefore, the sinogram 320 represents an expanded FOV that is greater than the acquisition FOV represented by the sinogram 250 of FIG. 7. Because the rebinned samples are in parallel geometry, only $\pi$ projection angle is needed for reconstruction of the cardiac data. This allows nearly 57 degrees of angular shift, corresponding to approximately 55 msec (for 0.35 seconds per gantry revolution) of temporal window adjustment if needed. As discussed previously, if the heart rate varies greatly, the acquisition window may be increased by increasing the angular range to be greater than $\pi+2\gamma_m$, which will allow an even greater temporal window adjustment.

It should be understood that the methods of FIGS. 3 and 9 may be embodied in the set of instructions of a computer program that may be executed by one or more processors of the CT system 10. Additionally, the computer program may be stored on a computer readable storage medium, such as a CD, or embodied in a computer data signal that is downloadable to the CT system 10.

A technical effect of at least one embodiment is optimizing gating when combining volumes of data that image structures undergoing physiological motion. The optimizing is based on differences between images of different volumes. Reconstructed images from an overlapped portion of consecutive volumes of data may be compared to one another to determine the best phase match prior to joining the volumes. By acquiring data over an angular range that corresponds to a FOV that is greater than the region comprising the anatomical structure of interest, such as the actual cardiac region, consecutive volumes of data may be shifted temporally with respect to each other. The temporal shift allows images acquired using a fixed acquisition window to be reconstructed at different motion phases even though the original acquisition is limited to a single phase. In addition, a motion signal, such as the ECG signal, breath cycle, or other physiological signal, may be evaluated prior to acquiring patient data to determine if a greater angular range is needed to allow greater temporal window adjustment.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A method for reconstructing images of structures undergoing physiological motion, comprising:
    acquiring a first volume of data over a first motion cycle, the first volume comprising a first overlap volume;
    acquiring a second volume of data over a second motion cycle, the second volume comprising a second overlap volume, the first and second overlap volumes comprising a same anatomical region with respect to each other;
    selecting at least one time $t_1$ for the data of the first overlap volume;
    reconstructing at least one image associated with the at least one time $t_1$;
    forming, using a processor, a reconstructed volume of data based on temporal data for the first and second overlap volumes using a difference in the same anatomical region corresponding to a difference in a mechanical state of the anatomical region in images of the first and second overlap regions, including comparing at least two images from within the second overlap volume to the at least one image to identify a set of images that have a minimum difference there-between, the reconstructed volume being based on the set of images.

2. The method of claim 1, further comprising calculating a total difference function based on the first and second overlap volumes, the reconstructed volume being further based on the total difference function.

3. The method of claim 1, further comprising:
    calculating a two-dimensional curve of total difference functions based on predetermined times within the first and second overlap volumes; and
    identifying a minimum value along the two-dimensional curve to identify a phase match between the first and second volumes of data.

4. The method of claim 1, further comprising:
    determining a temporal shift based on times associated with the set of images that have the minimum difference, the reconstructed volume being based on the temporal shift.

5. The method of claim 1, wherein the first and second volumes of data comprise Computed Tomography (CT) data, the method further comprising:
    acquiring electrocardiogram (ECG) data; and
    adjusting an angular range associated with acquiring the first and second volumes of data based on the ECG data.

6. The method of claim 1, wherein the first and second volumes of data comprise CT data, the method further comprising acquiring the first and second volumes of data using a step-and-shoot acquisition technique.

7. The method of claim 1, wherein the second volume of data further comprises a third overlap volume, the method farther comprising:
    acquiring a third volume of data over a third motion cycle, the third volume of data comprising at least a fourth overlap volume, the third and fourth overlap volumes comprising like anatomical regions with respect to each other;
    determining a first temporal shift based on a comparison of images from within the first and second overlap volumes; and
    determining a second temporal shift based on a comparison of images from within the third and fourth overlap volumes, the reconstructed volume being formed to minimize an overall temporal shift that is based on the first and second temporal shifts.

8. The method of claim 1, wherein the difference in the mechanical state of the anatomical region is not determined from an electrocardiography signal.

9. The method of claim 1, wherein the anatomical region is a heart and the mechanical state of the heart comprises a physiological motion of the heart.

10. The method of claim 9, further comprising identifying images that have a least amount of difference within a plurality of motion cycles of the heart determined by when the physiological motion of the heart is closest to the same in a one or more images of the first and second overlap volumes.

11. The method of claim 1, further comprising comparing the anatomical region in the first and second overlap volumes for the first and second motion cycles to identify a physiological difference therebetween and using the physiological difference to form the reconstructed volume of data.

12. The method of claim 11, further comprising identifying a least physiological difference therebetween.

13. A Computed Tomography (CT) system for acquiring data, comprising:
    an x-ray source configured to project x-rays at a subject to be scanned;
    an x-ray detector array configured to detect x-rays projected by the x-ray source and attenuated by the subject;
    a table configured to hold the subject with respect to the x-ray source and the x-ray detector; and
    a computer configured to:
        acquire a first volume of data over a first motion cycle;
        acquire a second volume of data over a second motion cycle, the first and second volumes having first and second overlap volumes, respectively, the first and second overlap volumes comprising common anatomical region data of the subject; and
        combine the first and second volumes based on temporal data for the first and second overlap volumes using a difference between the same anatomical region corresponding to a difference in a mechanical state of the anatomical region in images of the first and second overlap regions, including temporally shifting at least one of the first and second volumes based on a minimum difference between images from within the first and second overlap volumes.

14. The system of claim 13, wherein the table is stationary while the first and second volumes are acquired.

15. The system of claim 13, wherein the first and second motion cycles are first and second cardiac cycles, respectively, and wherein the first and second volumes of data are acquired over an angular range that corresponds to a field of view (FOV) that is larger than a cardiac region within the subject.

16. The system of claim 13, wherein the first and second volumes of data are acquired over an angular range that corresponds to an acquisition FOV, the computer further configured to:
- perform row-wise cone-to-parallel rebinning on measured samples associated with the first and second volumes of data to form rebinned data; and
- perform a zero$^{th}$ order extrapolation based on the rebinned data to form an expanded FOV that is greater than the acquisition FOV.

17. The system of claim 13, the computer further configured to:
- perform rebinning and extrapolation on measured samples of the first and second volumes of data to form an expanded FOV that is greater than an acquisition FOV associated with the first and second volumes of data; and
- temporally shift at least one of the first and second volumes within the expanded FOV to match a phase within the first and second motion cycles based on the first and second overlap volumes, the first and second volumes being combined based on the temporal shift.

18. The system of claim 13, further comprising an ECG apparatus for acquiring ECG data from the subject, the computer further configured to acquire the first and second volumes of data over an angular range based on the ECG data.

19. A method for acquiring images of a subject, comprising:
- acquiring at least two volumes of data comprising data for at least a portion of a structure undergoing physiological motion, each of the at least two volumes of data being acquired over different physiological motion cycles, each of the at least two volumes of data comprising a portion that has common anatomical data with an adjacent volume of data to define at least first and second overlap volumes of the at least two volumes;
- comparing, using a processor, the at least first and second overlap volumes that have common anatomical data to one another to identify images within the first and second overlap volumes having a match between the motion cycles associated with the at least first and second overlap volumes identified by a minimum difference between images from within the first and second overlap volumes; and
- combining, using a processor, the at least two volumes of data by temporally shifting at least one of the two volumes based on the minimum difference between the first and second overlap volumes.

20. The method of claim 19, wherein the at least two volumes of data comprise measured samples, the method further comprising rebinning and extrapolating the measured samples prior to identifying the at least one temporal shift.

21. The method of claim 19, wherein the comparing further comprises determining a minimum difference between the first and second overlap volumes.

22. The method of claim 19, further comprising comparing third and fourth overlap volumes that have common anatomical data to one another to identify a second temporal shift indicating an other match between the motion cycles associated with the third and fourth overlap volumes, the combining being further based on the second temporal shift.

* * * * *